US00PP12903P2

(12) United States Plant Patent
Moerman

(10) Patent No.: US PP12,903 P2
(45) Date of Patent: Sep. 3, 2002

(54) ASTER PLANT NAMED 'CHELSEA'

(75) Inventor: Marcel Moerman, De Lier (NL)

(73) Assignee: Moerselect B.V., De Lier (NL)

( * ) Notice: Subject to any disclaimer, the term of this patent is extended or adjusted under 35 U.S.C. 154(b) by 46 days.

(21) Appl. No.: 09/592,374

(22) Filed: Jun. 12, 2000

(51) Int. Cl.[7] ..... A01H 5/00
(52) U.S. Cl. ..... Plt./355
(58) Field of Search ..... Plt./355

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Aster plant named 'Chelsea', characterized by its vigorous and strong growth; rapid growth rate; bright green leaves; numerous inflorescences per flowering stem; white-colored ray florets; and good postproduction longevity.

1 Drawing Sheet

BACKGROUND OF THE INVENTION

The present Invention relates to a new and distinct cultivar of Aster plant, botanically known as *Aster novi-belgii* and referred to by the cultivar name Chelsea.

The new Aster is a product of a planned breeding program conducted by the Inventor in De Lier, The Netherlands. The objective of the breeding program was to develop new strong-growing cut flower Aster cultivars with attractive floret colors. The new Aster originated from a cross made by the Inventor of a proprietary Aster selection identified as code number 268, not patented, as the female, or seed, parent with a proprietary Aster selection identified as code number 1198, not patented, as the male, or pollen, parent. The new Aster was selected by the Inventor on the basis of its large inflorescence size and attractive ray floret color. Plants of the female parent selection 268 and plants of the new Aster differ in inflorescence size, leaf size and leaf color. Plants of the male parent selection 1198 and plants of the new Aster differ in ray floret color and leaf size.

Asexual reproduction of the new cultivar by terminal cuttings taken in De Lier, The Netherlands has shown that the unique features of this new Aster are stable and reproduced true to type in successive generations.

SUMMARY OF THE INVENTION

The following traits have been repeatedly observed and are determined to be the unique characteristics of 'Chelsea'. These characteristics in combination distinguish 'Chelsea' as a new and distinct cultivar:

1. Vigorous and strong growth; rapid growth rate.
2. Bright green leaves.
3. Numerous inflorescences per flowering stem.
4. White-colored ray florets.
5. Good postproduction longevity.

Compared to plants of the Aster cultivar Monte Cassino, not patented, plants of the new Aster have larger inflorescences, longer flowering stems and lorger leaves.

The cultivar Chelsea has not been observed under all possible environmental conditions. The phenotype may vary somewhat with variations in environment such as temperature, daylength and light intensity, without, however, any variance in genotype.

BRIEF DESCRIPTION OF THE PHOTOGRAPH

The accompanying colored photograph illustrates the overall appearance of the new Aster, showing the colors as true as it is reasonably possible to obtain in colored reproductions of this type. Colors in the photograph may differ slightly from the color values cited in the detailed botanical description which more accurately describe the actual colors of the new Aster. The photograph comprises a side perspective view of a typical flowering stem of the new Aster.

DETAILED BOTANICAL DESCRIPTION

The following observations, measurements and values describe flowering plants of the new Aster grown in De Lier, The Netherlands, under conditions which approximate commercial cut Aster production in a glass-covered greenhouse. Plants used in the photographs and the description were about 12 weeks old. Color references are made to The Royal Horticultural Society Colour Chart except where general terms of ordinary dictionary significance are used.

Botanical classification: *Aster novi-belgii* cultivar Chelsea.
Parentage:
- *Female, or seed, parent*.—Proprietary selection of *Aster novi-belgii* identified as code number 268, not patented.
- *Male, or pollen, parent*.—Proprietary selection of *Aster novi-belgii* identified as code number 1198, not patented.

Propagation:
- *Type*.—By terminal cuttings.
- *Time to initiate roots, summer*.—About 14 days at 18° C.
- *Time to initiate roots, winter*.—About 21 days at 18° C.
- *Time to develop roots, summer*.—About 21 days at 18° C.
- *Time to develop roots, winter*.—About 28 days at 18° C.
- *Rooting habit*.—Thick and freely branching.

Plant description:
- *Appearance*.—Herbaceous flowering plant used for cut flowers. Stems upright; basally branching; flowering stems, pyramidal in overall shape. Very freely flowering with numerous inflorescences per flowering stem; white-colored ray florets and yellow-colored disc florets.

*Crop time*.—From planting rooted cuttings, about 12 weeks are required to harvesting of flowering stems.

*Branching habit*.—Freely branching; typically about five lateral branches develop after pinching (removal of terminal apex).

*Vigor*.—Vigorous and strong growth; rapid growth rate.

*Plant height*.—About 1 m.

*Plant diameter or spread*.—About 25 cm.

*Lateral branches* (*flowering*).—Length: About 1 m. Diameter or spread: About 10 cm. Internode length: About 1.75 cm. Texture: Glabrous, smooth. Color: 137B.

*Foliage description*.—Leaves alternate, single; sessile. Length: About 8 cm. Width: About 7 mm. Shape: Roughly lanceolate. Apex: Pointed. Base: Attenuate. Margin: Slightly serrated. Texture: Smooth. Color: Young foliage, upper surface: 137A. Young foliage, lower surface: 137B. Fully expanded foliage, upper surface: 137A; veins, 137A. Fully expanded foliage, lower surface: 137B; veins, 137B.

Inflorescence description:

*Appearance*.—Composite inflorescence form. Disc and ray florets arranged acropetally on a capitulum. Inflorescences displayed upright on peduncles arising from upper leaf axils. Floriferous with typically about 120 inflorescence buds and open inflorescences per lateral stem and about 600 inflorescence buds and open infloresences per plant.

*Flowering response*.—Short day responsive; under natural photoperiodic conditions, plants flower in the autumn. Flowering can be induced under short day/long night conditions at other times of the year. Response time is about six weeks.

*Post-production longevity*.—Inflorescences last about two weeks as a cut flower and about two weeks on the plant. Inflorescences persistent.

*Fragrance*.—Not detected.

*Inflorescence bud*.—Length: About 5 mm. Diameter: About 4 mm. Shape: Oblong. Time to opening: About three days.

*Inflorescence size*.—Diameter: About 2 cm. Depth (height): About 1 cm. Diameter of disc: About 7 mm.

*Ray florets*.—Number of rows: Typically one per inflorescence. Length: About 1 cm. Width: About 3 mm. Shape: Oblong. Apex: Pointed. Base: Oblong. Margin: Entire. Aspect: Mostly flat. Texture: Smooth, satiny. Color: When opening, upper surface: 155D. When opening, lower surface: 155D. Fully opened, upper surface: 155D. Fully opened, lower surface: 155D.

*Disc florets*.—Shape: Tubular. Number of disc florets per inflorescence: About 60. Length: About 5 mm. Diameter: About 2 mm. Color: Immature: 6B. Mature: 8B.

*Phyllaries*.—Shape: Linear. Apex: Pointed. Margin: Entire. Texture: Smooth. Color, upper and lower surfaces: 137B.

*Peduncle*.—Aspect: Angled about 45° to the stem. Strength: Strong. Texture: Smooth. Color: 137B.

*Reproductive organs*.—Androecium: Present on disc florets only. No pollen observed. Gynoecium: Present on ray and disc florets.

*Seed*.—Seed development has not been observed.

Disease resistance: Resistance to pathogens common to Aster has not been observed on plants of the new Aster.

It is claimed:

1. A new and distinct cultivar of Aster plant named 'Chelsea', as illustrated and described.

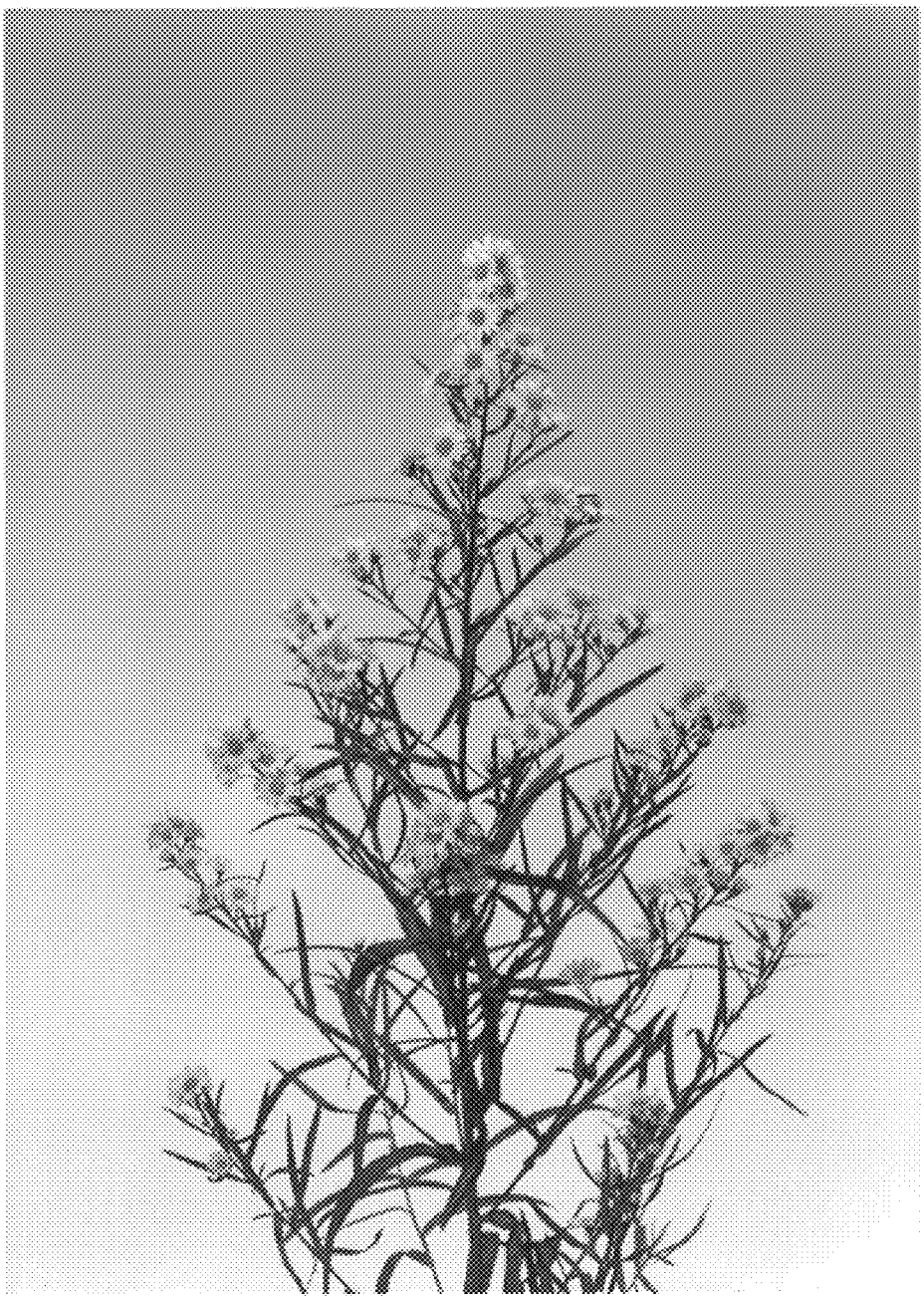

* * * * *